(12) United States Patent
Yonejima et al.

(10) Patent No.: US 10,507,222 B2
(45) Date of Patent: Dec. 17, 2019

(54) LACTIC ACID BACTERIUM AND COMPOSITION INCLUDING SAID LACTIC ACID BACTERIUM

(71) Applicant: NITTO PHARMACEUTICAL INDUSTRIES, LTD., Muko-shi, Kyoto (JP)

(72) Inventors: Yasunori Yonejima, Muko (JP); Keiko Hisa, Muko (JP); Yoshie Uchibori, Muko (JP)

(73) Assignee: NITTO PHARMACEUTICAL INDUSTRIES, LTD., Muko (JP)

( * ) Notice: Subject to any disclaimer, the term of this patent is extended or adjusted under 35 U.S.C. 154(b) by 289 days.

(21) Appl. No.: 15/314,829

(22) PCT Filed: May 28, 2015

(86) PCT No.: PCT/JP2015/002715
§ 371 (c)(1),
(2) Date: Nov. 29, 2016

(87) PCT Pub. No.: WO2015/182155
PCT Pub. Date: Dec. 3, 2015

(65) Prior Publication Data
US 2017/0202890 A1    Jul. 20, 2017

(30) Foreign Application Priority Data

May 29, 2014   (JP) ................. 2014-110912

(51) Int. Cl.
*A61K 35/747* (2015.01)
*A23L 33/135* (2016.01)
*C12R 1/24* (2006.01)
*A61K 35/00* (2006.01)

(52) U.S. Cl.
CPC .......... *A61K 35/747* (2013.01); *A23L 33/135* (2016.08); *C12R 1/24* (2013.01); *A23V 2002/00* (2013.01); *A61K 2035/11* (2013.01)

(58) Field of Classification Search
None
See application file for complete search history.

(56) References Cited

U.S. PATENT DOCUMENTS

2010/0150890 A1    6/2010  Beppu et al.

FOREIGN PATENT DOCUMENTS

| CA | 2851018 A1 | 6/2009 |
| EP | 1649863 A1 | 4/2006 |
| JP | 2011-201801 A | 10/2011 |
| WO | WO 2003/055984 A1 | 7/2003 |
| WO | WO 2004/112809 A1 | 12/2004 |

OTHER PUBLICATIONS

Japanese Patent Office, International Search Report in International Patent Application No. PCT/JP2015/002715 (dated Aug. 18, 2015).

*Primary Examiner* — Robert A Zeman
(74) *Attorney, Agent, or Firm* — Leydig, Voit & Mayer, Ltd.

(57) ABSTRACT

The present invention provides a *lactobacillus* that improves hyperuricemia, fatty liver and a lifestyle-related disease, and a composition containing the *lactobacillus*.

6 Claims, 6 Drawing Sheets
Specification includes a Sequence Listing.

LACTIC ACID BACTERIUM AND COMPOSITION INCLUDING SAID LACTIC ACID BACTERIUM

CROSS-REFERENCE TO RELATED APPLICATIONS

This patent application is the U.S. national phase of International Patent Application No. PCT/JP2015/002715, filed on May 28, 2015, which claims the benefit of Japanese Patent Application No. 2014-110912, filed May 29, 2014, the disclosures of which are incorporated herein by reference in their entireties for all purposes.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 2,450 bytes ASCII (Text) file named "727212SequenceListing.txt," created Nov. 28, 2016.

TECHNICAL FIELD

The present invention relates to *Lactobacillus brevis* having plural functions, particularly *Lactobacillus brevis* NTM003 strain deposited under deposit number NITE BP-01634, and a composition, particularly a pharmaceutical product, a food and the like, containing the same.

BACKGROUND ART

Hyperuricemia refers to a state showing a high level of uric acid in blood, which is caused by decreased uric acid excretion and excessive uric acid production due to a genetic factor or an environmental factor. Hyperuricemia is known to cause complications represented by gout as well as renopathy, urinary calculosis and the like. It is said that 5 million people are at risk of developing gout across Japan at present, and the peak of the age of onset is becoming earlier from 50's in the past to 30's, and prophylaxis and treatment of hyperuricemia is drawing attention.

The prophylaxis and treatment of hyperuricemia is performed by controlling blood uric acid level by a combination of life guidance (elimination of obesity, diet therapy, restriction of alcohol intake, avoidance of excessive motility, stress reduction) and medication therapy. Improvement of life style by life guidance affords an effect of improving hyperuricemia; however, control of life style for a long term is not easy. When a mediation therapy is necessary, blood uric acid level is controlled by a doctor. When the symptoms of patients who do not require mediation yet are to be improved by life guidance, a method of decreasing absorption of purine body into the body by decomposing the purine body in the intestine by oral ingestion of microorganism such as lactic acid bacterium and yeast that decompose purine body, and the like to the patients has been reported as a life guidance aiding method (patent document 1). Lactic acid bacterium is a microorganism widely utilized from long ago for foods such as yoghurt, pickles and the like, and pharmaceutical products, and there is only a little concern about side effects even when ingested for a long term. Therefore, ingestion of lactic acid bacterium can be a useful method for the prophylaxis or treatment of hyperuricemia.

Fatty liver is a state of excessive accumulation of fat in the liver, and medically indicates a state wherein fat vacuoles are found in not less than 30% of the hepatocytes in the liver. Fatty liver is largely divided into alcoholic fatty liver and non-alcoholic fatty liver, and 12-36 million people are said to have developed non-alcoholic fatty liver or steatohepatitis in Japan. The cause of non-alcoholic fatty liver includes, for example, obesity, diabetes, hyperlipidemia, malnutrition and the like. Fatty liver scarcely shows subjective symptoms, and an early treatment is necessary since transfer to hepatitis, cirrhosis and liver cancer has been reported.

For prophylaxis or treatment of fatty liver, cutting down on drinking and abstinence are most effective for alcoholic fatty liver, and improvement of life style by diet therapy, motility therapy and the like is necessary for non-alcoholic fatty liver. Particularly, non-alcoholic fatty liver caused by diabetes also requires medication therapy. While improvement of life style is effective for the prophylaxis or treatment of fatty liver, it is not easy to improve irregular life style, unbalanced diet and lack of exercise. Therefore, a safe and burdenless method for supporting improvement of life style is desired. Heretofore, an agent for the prophylaxis and/or inhibition of fatty liver by lactic acid bacterium with less concern about side effects has been disclosed (patent document 2).

However, the lactic acid bacteria disclosed in the above-mentioned patent documents are separate lactic acid bacteria each having the function of a serum uric acid level reducer or agent for the prophylaxis and/or inhibition of fatty liver, and a lactic acid bacterium concurrently having a function to improve hyperuricemia and fatty liver has not been reported yet.

DOCUMENT LIST

Patent Documents patent document 1: WO 2004/112809
patent document 2: JP-A-2011-201801

SUMMARY OF THE INVENTION

Problems to be Solved by the Invention

In view of the above-mentioned situation, an object of the present invention is to provide a lactic acid bacterium that can be used for foods and pharmaceutical products that can prevent or treat hyperuricemia and fatty liver, and further, lifestyle-related diseases. Simultaneously, an object of the present invention is to provide a composition, particularly a pharmaceutical product or food, for the prophylaxis and/or treatment of hyperuricemia, fatty liver and lifestyle-related diseases.

Means of Solving the Problems

The present inventors have conducted intensive studies in an attempt to solve the aforementioned problems and selected a lactic acid bacterium having a remarkably high nucleoside-degradation potential. The selected lactic acid bacterium was orally administered to a rat raised on a purine body-containing feed, and an influence on the serum uric acid level of the rat was observed. In addition, an influence on the blood uric acid level when a capsule containing the lactic acid bacterium was ingested by a human having a comparatively high (not less than 6.5 mg/dL) blood uric acid level was observed. As a result, novel *Lactobacillus brevis* NTM003 that significantly suppresses an increase in the uric acid level was found. Furthermore, the present inventors gave the above-mentioned *lactobacillus* to a mouse model of obesity together with a high-fat diet, and the liver weight and liver lipid content were measured 42 days later. As a result, it was found that the *lactobacillus* administration group has a significantly low liver weight and an increase in the liver lipid content is suppressed as compared to a group without administration of the above-mentioned *lactobacillus*.

The present invention was completed based on the above findings.

Accordingly, the present invention is as follows:

[1] *Lactobacillus* (NITE BP-01634) which is *Lactobacillus brevis* NTM003 strain, or a processed bacterium thereof.
[2] A composition for suppressing or improving an increase in the blood uric acid level, comprising the *lactobacillus* or a processed bacterium thereof of the above-mentioned [1] as an active ingredient.
[3] A composition for suppressing or improving fatty liver, comprising the *lactobacillus* or a processed bacterium thereof of the above-mentioned [1] as an active ingredient.
[4] A composition for suppressing or improving a lifestyle-related disease, comprising the *lactobacillus* or a processed bacterium thereof of the above-mentioned [1] as an active ingredient.
[5] The composition of any one of the above-mentioned [2]-[4], which is a pharmaceutical product.
[6] The composition of any one of the above-mentioned [2]-[4], which is a food.
[7] A method of suppressing or improving an increase in the blood uric acid level, fatty liver or a lifestyle-related disease, comprising administering an effective amount of *lactobacillus* (NITE BP-01634), which is *Lactobacillus brevis* NTM003 strain, or a processed bacterium thereof to a subject.
[8] The method of the above-mentioned [7], wherein the *lactobacillus* (NITE BP-01634), which is *Lactobacillus brevis* NTM003 strain, or a processed bacterium thereof is orally administered at $1 \times 10^4$-$1 \times 10^{12}$ cells or an amount equivalent thereto per day to a patient with a high blood uric acid level, a fatty liver patient or a lifestyle-related disease patient.

Effect of the Invention

In the present invention, *Lactobacillus brevis* NTM003 strain (NITE BP-01634) (hereinafter the *lactobacillus* of the present invention) was found to be a conventionally unknown *lactobacillus* having an action to suppress an increase in or improve a blood uric acid level and an action to suppress or improve fatty liver in combination. The *lactobacillus* of the present invention is industrially extremely useful since, based on the aforementioned functions, it is utilized for the improvement or prophylaxis of lifestyle-related diseases, and can be used in the fields of pharmaceutical product, food and the like with the aim to particularly improve hyperuricemia which causes gout and renopathy when it progresses, and fatty liver which causes hepatitis and the like.

DESCRIPTION OF EMBODIMENTS

Figure 1:
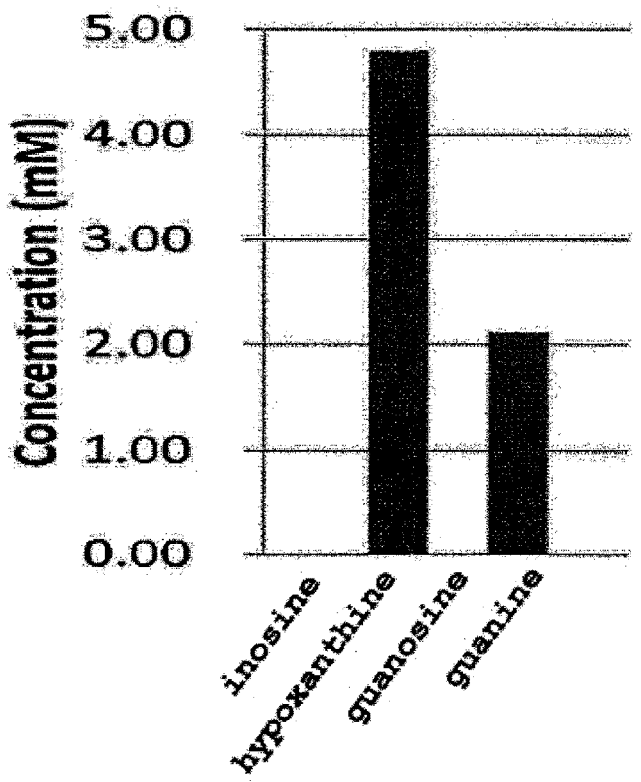
FIG. 1 shows nucleoside degradation by NTM003 strain.

The present invention is explained in detail below.

The present invention provides *Lactobacillus brevis* NTM003 strain effective for the prophylaxis or improvement of hyperuricemia and fatty liver. The *lactobacillus* of the present invention was deposited on Jun. 11, 2013 at Incorporated Administrative Agency National Institute of Technology and Evaluation Patent Microorganisms Depositary, 2-5-8 Kazusakamatari, Kisarazu-shi, Chiba, Japan. The accession No. of NTM003 strain is NITE BP-01634.

The *lactobacillus* of the present invention can be cultured according to a conventional method of lactic acid bacterium culture. While the medium to be used for the culture is not particularly limited as long as the *lactobacillus* of the present invention can grow therein, the *lactobacillus* can be cultured in a medium for lactic acid bacterium culture (solid medium, liquid medium etc.) such as MRS medium and the like. The medium may contain various vitamins (vitamin A, vitamin B1, vitamin B2, vitamin B6, vitamin C, vitamin D, vitamin E etc., and derivatives thereof), various amino acids (including natural amino acid and synthetic amino acid), nucleic acid bases (purine, pyrimidine), inorganic salts ($MgSO_4$, $MnSO_4$, $FeSO_4$, NaCl etc.) and the like as necessary. As the culture conditions, culture temperature, culture period, and pH of medium can be appropriately adjusted. For example, the culture temperature is generally 30-37° C., preferably 35-37° C. The culture period is generally 16 hr-3 days, preferably 1-2 days. The pH of the medium is generally pH3-8, preferably pH 4-7. The culture may be standing culture or, when the medium is a liquid medium, stirring culture. In addition, the culture may be aerobic or anaerobic.

The *lactobacillus* of the present invention was separated from pickles of rape blossoms.

The mycological properties of the *lactobacillus* of the present invention are shown below.

(1) cell form
   bacillus
(2) motility
   none
(3) spore formation
   not formed
(4) visual characteristics of colony on agar medium
   white colony with circular shape is formed on MRS agar medium
(5) Gram staining
   positive
(6) growth temperature
   grows well at 30-37° C.

The sugar assimilability of the *lactobacillus* of the present invention is shown in Table 1.

TABLE 1

| # | Substrate | Result |
|---|---|---|
| 0 | control | − |
| 1 | glycerol | − |
| 2 | erythritol | − |
| 3 | D-arabinose | − |
| 4 | L-arabinose | + |
| 5 | ribose | + |
| 6 | D-xylose | + |
| 7 | L-xylose | − |
| 8 | adonitol | − |
| 9 | β-methyl-D-xyloside | − |
| 10 | galactose | − |
| 11 | glucose | + |
| 12 | fructose | + |
| 13 | mannose | − |
| 14 | sorbose | − |
| 15 | rhamnose | − |
| 16 | dulcitol | − |
| 17 | inositol | − |
| 18 | mannitol | − |
| 19 | sorbitol | − |
| 20 | α-methyl-D-mannoside | − |
| 21 | α-methyl-D-glucoside | − |
| 22 | N-acetylglucosamine | + |
| 23 | amygdalin | − |
| 24 | arbutin | − |
| 25 | esculin | + |
| 26 | salicin | − |
| 27 | cellobiose | − |
| 28 | maltose | + |
| 29 | lactose | − |
| 30 | melibiose | + |
| 31 | saccharose | − |
| 32 | trehalose | − |
| 33 | inulin | − |
| 34 | melezitose | − |
| 35 | raffinose | − |
| 36 | starch | − |
| 37 | glycogen | − |
| 38 | xylitol | − |
| 39 | gentiobiose | − |
| 40 | D-turanose | − |
| 41 | D-lyxose | − |
| 42 | D-tagatose | − |
| 43 | D-fucose | − |
| 44 | L-fucose | − |
| 45 | D-arabitol | − |
| 46 | L-arabitol | − |
| 47 | gluconate | + |
| 48 | 2-keto-gluconate | + |
| 49 | 5-keto-gluconate | + |

+: positive
−: negative

Furthermore, the *lactobacillus* of the present invention has 16S rRNA shown in SEQ ID NO: 1. From the various properties and characteristics above and in light of Bergey's Manual of Systematic Bacteriology, the *lactobacillus* strain of the present invention can be identified as a strain belonging to *Lactobacillus brevis*.

As in the below-mentioned Examples, in the *lactobacillus* of the present invention, inosine and guanosine, which are purine bodies in a substrate solution, have been converted to different purine bodies, hypoxanthine and guanine, respectively. A purine body is a compound having a purine skeleton, and includes purine nucleotide (adenylic acid, deoxyadenylic acid, guanylic acid, deoxyguanylic acid), purine nucleoside (adenosine, deoxyadenosine, guanosine, deoxyguanosine), purine base (adenine, guanine), oligonucleotide and polynucleotide containing a purine base and the like. A purine base constitutes a nucleic acid, as well as various biological components such as ATP, GTP, cAMP, cGMP, coenzyme A, FAD, NAD and the like, and such biological components are also all included in the purine body as long as they have a purine skeleton.

Unnecessary purine body in the body is finally metabolized to uric acid and excreted. The metabolism pathway of purine body until it reaches uric acid is widely known, wherein AMP becomes adenosine by 5'-nucleosidase, and adenosine is metabolized to hypoxanthine via inosine. GMP becomes guanosine by 5'-nucleosidase, and then metabolized to guanine. Furthermore, hypoxanthine is metabolized to xanthine by xanthineoxydase, and guanine is metabolized to xanthine by guanine deaminase, and finally, xanthine is metabolized to uric acid by xanthineoxydase. Therefore, one of the effective means for suppressing or improving an increase in the blood uric acid level is to suppress the amount of purine body absorbed in the body from the intestine. It is known that the absorption efficiency thereof increases in the order of xanthine, guanine, guanosine, and in the order of hypoxanthine, inosine, adenosine.

Therefore, as in the below-mentioned Examples, in an attempt to suppress the amount of purine body absorption by converting inosine and guanosine having high absorption efficiency to hypoxanthine and guanine which are purine bodies having low absorption efficiency, the *lactobacillus* of the present invention was orally given to rats to find suppression of an increase in the serum uric acid level of the rats. In another Example, in the test subjects that orally ingested the *lactobacillus* of the present invention, a test subject having a high blood uric acid level showed a significant decrease in the level. Therefore, the *lactobacillus* of the present invention is a novel *lactobacillus* having a suppressive or improving effect on an increase in the blood uric acid level.

As in the below-mentioned another Example, oral ingestion of the *lactobacillus* of the present invention to a mouse model of obesity and/or diabetes suppressed an increase in the liver weight and liver lipid content of the mouse. Therefore, the *lactobacillus* of the present invention is a novel *lactobacillus* having a suppressive or improving effect on the fatty liver.

Based on an effect to suppress an increase in or improve a blood uric acid level and a suppressive/improving effect on fatty liver by the *lactobacillus* of the present invention, the present invention provides a composition for suppressing an increase in or improving a blood uric acid level/suppressing or improving fatty liver, which contains the *lactobacillus* of the present invention or a processed bacterium thereof as an active ingredient (hereinafter the composition of the present invention). Also, the composition of the present invention can also be applied to suppression/improvement of lifestyle-related diseases. In the present invention, the lifestyle-related diseases refer to a disease group in which life styles such as eating habits, exercise habits, rest, smoking, alcohol drinking and the like are involved in the onset and progression thereof, and include pathologies such as hyperuricemia, adult obesity, childhood obesity, malnutrition, anorexia, gout, hypertension, arteriosclerosis, kidney stones, myocardial infarction, angina pectoris, gastric ulcer, kidney disease, fatty liver, hepatitis, cirrhosis, liver cancer, lung cancer, cerebral apoplexy, cerebral infarction and the like.

As the active ingredient to be contained in the composition of the present invention, the *lactobacillus* of the present invention separated from a culture by a collecting means such as centrifugation and the like can be used. A processed bacterium of the *lactobacillus* of the present invention can also be used as the active ingredient to be contained in the composition of the present invention. The processed bacterium of the present invention includes the *lactobacillus* of the present invention treated by concentration, drying, freeze-drying and the like. In addition, not only a separated bacterium but also a bacterial disrupture product and a homogenate after removal of debris by centrifugation after bacterial disrupture can be used as the processed bacterium of the present invention. As the form of the culture, not only a culture obtained by culturing according to the aforementioned culture conditions and a culture obtained using a medium generally used for culturing lactic acid bacterium, but also dairy products such as cheese, fermented milk, lactic acid bacteria beverage and the like, and the like can also be used, and the *lactobacillus* of the present invention can be separated by a known means.

The composition of the present invention contains the above-mentioned *lactobacillus* of the present invention and the like as active ingredients, and can be formulated by adding excipient, binder, disintegrant, lubricant and the like, and selecting the form (solid, liquid etc.) as appropriate according to the use.

Examples of the excipient include animal and plant oils such as soybean oil, safflower oil, olive oil, germ oil, sunflower oil, beef tallow, sardine oil and the like, polyvalent alcohols such as polyethylene glycol, propylene glycol, glycerol, sorbitol and the like, surfactants such as sorbitan ester of fatty acid, sucrose ester of fatty acid, glycerin fatty acid ester, polyglycerol fatty acid ester and the like, purified water, lactose, starch, crystalline cellulose, D-mannitol, lecithin, gum arabic, sorbitol solution, carbohydrate solution and the like.

Examples of the binder include hydroxypropylmethylcellulose, hydroxypropylcellulose, gelatin, pregelatinized starch, polyvinylpyrrolidone, polyvinylalcohol and the like.

Examples of the disintegrant include carmellose calcium, carmellose sodium, croscarmellose sodium, crospovidone, low-substituted hydroxypropylcellulose, cornstarch and the like.

Examples of the lubricant include talc, hydrogenated vegetable oil, waxes, light anhydrous silicic acid and the like derived from naturally occurring substance and derivatives thereof, stearic acid, magnesium stearate, calcium stearate, aluminum stearate and the like.

The composition of the present invention can further contain a sweetener, a colorant, a pH adjuster, a flavor, various amino acids and the like. Also, a solid state product may be coated by a well-known method. A liquid may be dissolved or suspended in water or other suitable medium when ingested.

The composition of the present invention is provided as, for example, a pharmaceutical product, a food, a feed and the like, though it is not limited to these.

When the composition of the present invention is used as a pharmaceutical product (hereinafter the pharmaceutical product of the present invention), the dosage form of the pharmaceutical product of the present invention includes powder, granule, pill, soft capsule, hard capsule, tablet, chewable tablet, quick-disintegrating tablet, syrup, liquid, suspension, and the like. A preparation thereof is prepared according to a conventional method.

Examples of the pharmaceutical product of the present invention for oral administration include solid or liquid dosage form, specifically tablet (including sugar-coated tablet, film-coated tablet), pill, granule, powder, capsule (including soft capsule), syrup, emulsion, suspension and the like. Such compositions are produced by a known method, and may contain carrier, diluent or excipient generally used in the pharmaceutical field. As the carrier, excipient for tablet, lactose, starch, saccharose, magnesium stearate are used.

As the pharmaceutical product of the present invention for parenteral administration, injection, suppository and the like are used. A preparation method of injection includes suspending or emulsifying the *lactobacillus* of the present invention or a processed bacterium thereof of the present invention in an aseptic aqueous solution or oily solution generally used for injection. As an aqueous solution for injection, saline, isotonic solution containing glucose or other auxiliary agent and the like are used. As an oily solution, sesame oil, soybean oil and the like are used. A suppository for rectal administration can be prepared by mixing the *lactobacillus* of the present invention or a processed bacterium thereof with a general base for suppository.

The subject of administration of the pharmaceutical product of the present invention is, for example, human or other warm-blooded animal (e.g., mouse, rat, rabbit, sheep, swine, bovine, cat, dog, monkey, chicken and the like).

While the dose of the pharmaceutical product of the present invention varies depending on the subject of administration, target disease, symptom, administration route and the like, when it is used for, for example, the suppression/improvement of hyperuricemia in adult, generally $1\times10^4$-$1\times10^{12}$ cells, preferably $1\times10^6$-$1\times10^{11}$ cells, more preferably $1\times10^8$-$1\times10^{11}$ cells, or an equivalent amount thereof of the *lactobacillus* of the present invention or a processed bacterium thereof as a daily dose can be administered orally or parenterally. Plural divided portions may be administered per day. When the condition is particularly serious, the dose may be increased according to the symptom. When the pharmaceutical product of the present invention is administered for the suppression/improvement of fatty liver, or suppression/improvement of a lifestyle-related disease, in adults, the dose, administration route and number of days of administration similar to those mentioned above may be employed.

When the composition of the present invention is used as a food (hereinafter the food of the present invention), examples of the form of the food of the present invention include supplements (powder, granule, soft capsule, hard capsule, tablet, chewable tablet, quick-disintegrating tablet, syrup, liquid etc.), drinks (tea drinks, carbonic acid drinks, lactic acid drinks, sport drinks etc.), confectionery (gummy, jelly, gum, chocolate, cookie, candy etc.), oil, fats and oils food (mayonnaise, dressing, butter, cream, margarine etc.), and the like.

The above-mentioned foods can contain, where necessary, various nutrients, various vitamins (vitamin A, vitamin B1, vitamin B2, vitamin B6, vitamin C, vitamin D, vitamin E, vitamin K etc.), various minerals (magnesium, zinc, iron, sodium, potassium, selenium etc.), dietary fiber, dispersing agent, stabilizer such as emulsifier and the like, sweetener, flavor components (citric acid, malic acid etc.), flavor, royal jelly, propolis, *Agaricus* and the like.

While the daily ingestion amount of the food of the present invention varies depending on the subject that ingests the food, target disease, symptom and the like, for example, when it is ingested for the suppression/improvement of hyperuricemia in adults, generally $1\times10^4$-$1\times10^{12}$ cells, preferably $1\times10^6$-$1\times10^{11}$ cells, more preferably $1\times10^8$-$1\times10^{11}$ cells, or an equivalent amount thereof of the *lactobacillus* of the present invention or a processed bacterium thereof as a daily ingestion amount can be ingested orally. Plural divided portions may be ingested per day. When the condition is particularly serious, the dose may be increased according to the symptom. When the food of the present invention is ingested for the suppression/improvement of fatty liver, or suppression/improvement of a lifestyle-related disease, in adults, the ingestion amount, ingestion route and number of days of ingestion similar to those mentioned above may be employed.

EXAMPLES

The present invention is explained in more detail in the following by referring to Examples. The Examples are mere exemplifications of the present invention and do not limit the scope of the present invention in any manner.

Example 1 In Vitro Test Relating to Uric Acid Level Decreasing Action of *Lactobacillus*

*Lactobacillus* NTM003 strain was inoculated to 15 mL of MRS medium (manufactured by BD), and cultured at 37° C. and collected. The obtained *lactobacillus* was set to a given turbidity ($OD_{600}$=0.1) with 0.85% NaCl and used as a sample solution. To the sample solutions were added a substrate solution (1 mL) (inosine 4 mM, guanosine 2 mM, 0.1 M KPB pH 7.0:$H_2O$=1:9), and the mixture was reacted anaerobically (37° C., 120 rpm, 1 hr), and the reaction mixture was analyzed by HPLC. Each analytical curve was drawn, and the concentration of nucleic acid contained in the reaction mixture was determined. The results thereof are shown in FIG. 1. Inosine and guanosine were not detected after the reaction for 1 hr, and hypoxanthine and guanine were detected.

Figure 2:
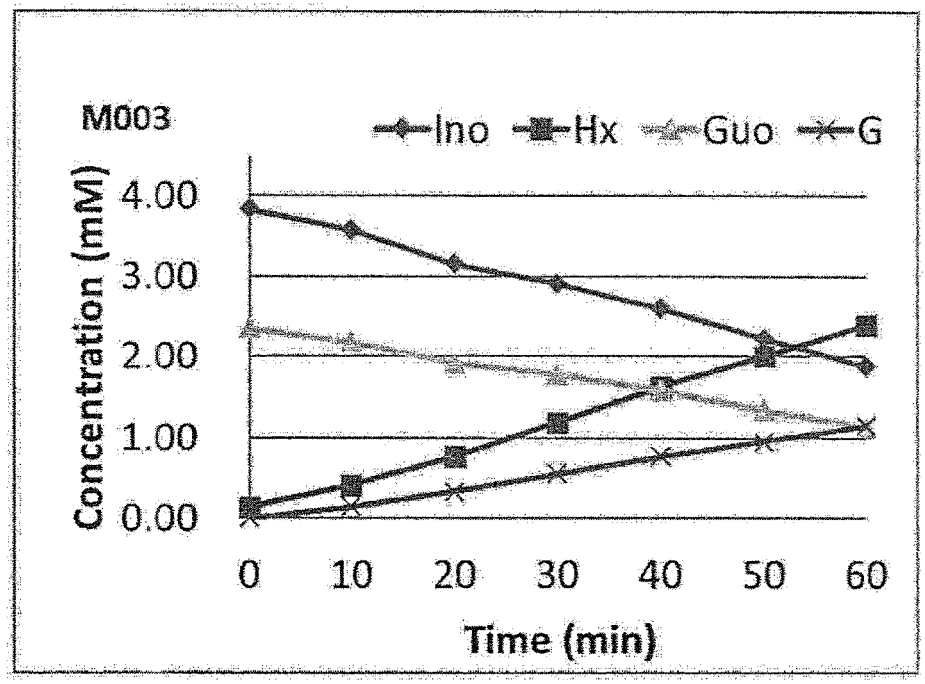
FIG. 2 shows time course changes of nucleoside degradation by NTM003 strain. Ino: inosine, Hx: hypoxanthine, Guo: guanosine, G: guanine

Furthermore, time-course changes of the NTM003 strain were examined. The amount of *lactobacillus* was the same as that in the above-mentioned sample solution, and the substrate solution was increased to 5 mL. The reaction mixture was stirred in an anaerobic chamber at 37° C., and fractionated every 10 min and analyzed by HPLC. The results are shown in FIG. 2. An increase in the resultant product along with a decrease in the substrate could be confirmed.

Example 2 In Vivo Test Relating to Uric Acid Level Decreasing Action of *Lactobacillus*

Production Example 1: Preparation of Powdered *Lactobacillus* and Preparation of Test Solution NTM003 strain was cultured at 37° C. in MRS medium (600 L) (manufactured by BD) or a medium (600 L) prepared to have the same composition as that of MRS medium, collected by centrifugation, and freeze-dried. The freeze-dried bacterium was pulverized by a grinding machine, and mixed with potato starch to give a powdered bacterium having a given concentration. As a test solution, the above-mentioned powdered *lactobacillus* (NTM003 strain) was suspended in the Japanese Pharmacopoeia water for injection at $5.51 \times 10^9$ cells/mL (prepared when in use).
(Preparation of Experiment Animal)
Rats (blister SPF, male, 7-week-old) were used. For breeding, an aluminum wire mesh bottom cage was used, and one rat was housed per cage. The illumination time was 12 hr/day (7:00-19:00).
(Quarantine and Acclimation)
After carrying in, the experiment animals were acclimated for 7 days. Health condition was confirmed on receipt of the animals, and the animals that showed no abnormality were housed in the breeding room, and raised in quarantine and acclimation for 7 days under breeding conditions and breeding environment similar to those in the below-mentioned test except the feed and the test solution.
(Feed and Mixed Feed)
Powder feed MF manufactured by Oriental Yeast Co., Ltd. was used. As a potassium oxonate mixed feed, powder feed MF was mixed with potassium oxonate (Sigma-Aldrich Ltd.) at 2.5 w/w %. As a potassium oxonate+RNA mixed feed, powder feed MF was mixed with potassium oxonate at 2.5 w/w % and RNA (MPbiomedical) at 1.0 w/w %.
(Grouping)
They were divided into 3 groups of control group, negative control group, and *lactobacillus* group, each group consisting of 8 animals. The constitution of the test groups are shown in Table 2.

TABLE 2

| test group | feed | | test solution | n | animal No. |
|---|---|---|---|---|---|
| control | — | | potassium oxonate | water for injection | 8 | 101-108 |
| negative control | RNA | potassium oxonate | water for injection | 8 | 201-208 |
| lactobacillus group | RNA | potassium oxonate | NTM003 strain | 8 | 301-308 |

Figure 3:
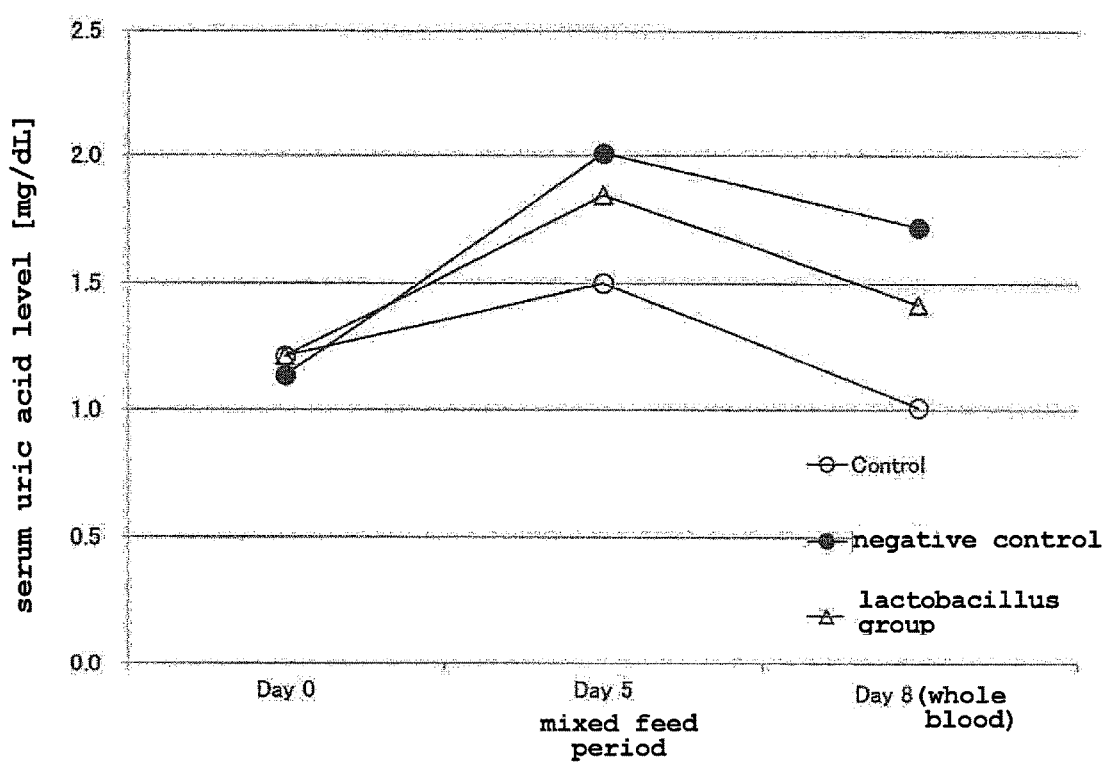
FIG. 3 shows changes in the serum uric acid level in a rat model of hyperuricemia.

(Breeding (Test))
After grouping as shown in Table 2, a potassium oxonate mixed feed (control group) and a potassium oxonate+RNA mixed feed (negative control group, *lactobacillus* group) were each freely given to rats for 8 days from a feeder. To the control group and negative control group, the Japanese Pharmacopoeia water for injection was forcedly administered at 1 mL/body once per day by using a stomach gavage needle, and to the *lactobacillus* group, the above-mentioned test solution was forcedly administered at 1 mL/body once per day by using a stomach gavage needle. The frequency of blood sample collection was before start of mixed feed free ingestion, on day 5 (1 hr after administration of test solution), and on day 8 (1 hr after administration of test solution). The blood was left standing at room temperature for not less than 30 min, centrifuged and the serum was collected. The serum was cryopreserved. The preserved serum was subjected to the measurement of the concentration of uric acid in the serum by using uric acid C-Test Wako (Wako Pure Chemical Industries, Ltd.).
(Test Results)
Abnormality was not found in the general state throughout 9 days of the observation period. All groups showed a satisfactory body weight gain. The control group, negative control group and *lactobacillus* group did not show difference in the feed ingestion amount. The results of the serum uric acid level are shown in FIG. 3. In the *lactobacillus* group, an increase in the serum uric acid level was suppressed as compared to the negative control group.

Example 3 Human Test Relating to Uric Acid Level Decreasing Action of *Lactobacillus*

(Preparation of Test Substance)
The *lactobacillus* powder prepared in Production Example 1 of Example 2 was filled in a food gelatin hard capsule at $2 \times 10^{10}$ CFU *lactobacillus* per capsule and used as a test substance.

(Test Subjects)

18 male and female adults (20's-60's)

(Test)

The test subjects ingested one capsule of the test substance per day for one month, and blood samples were collected before the start of ingestion and after ingestion for one month. The collected blood samples were measured for blood uric acid level by a clinical test company.

Figure 4:
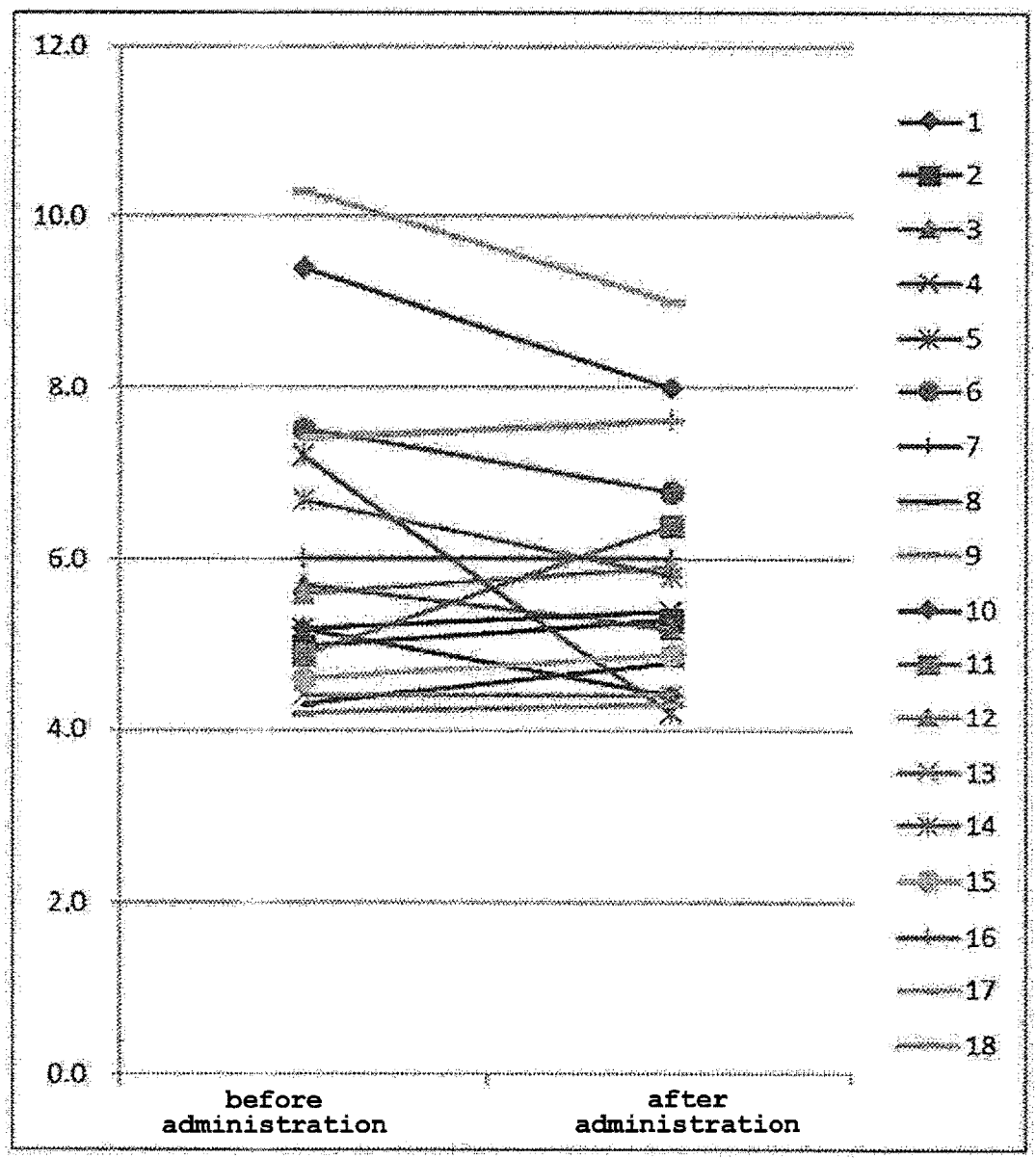
FIG. 4 shows the blood uric acid levels before and after ingestion of NTM003 strain in a human test.
Figure 5:
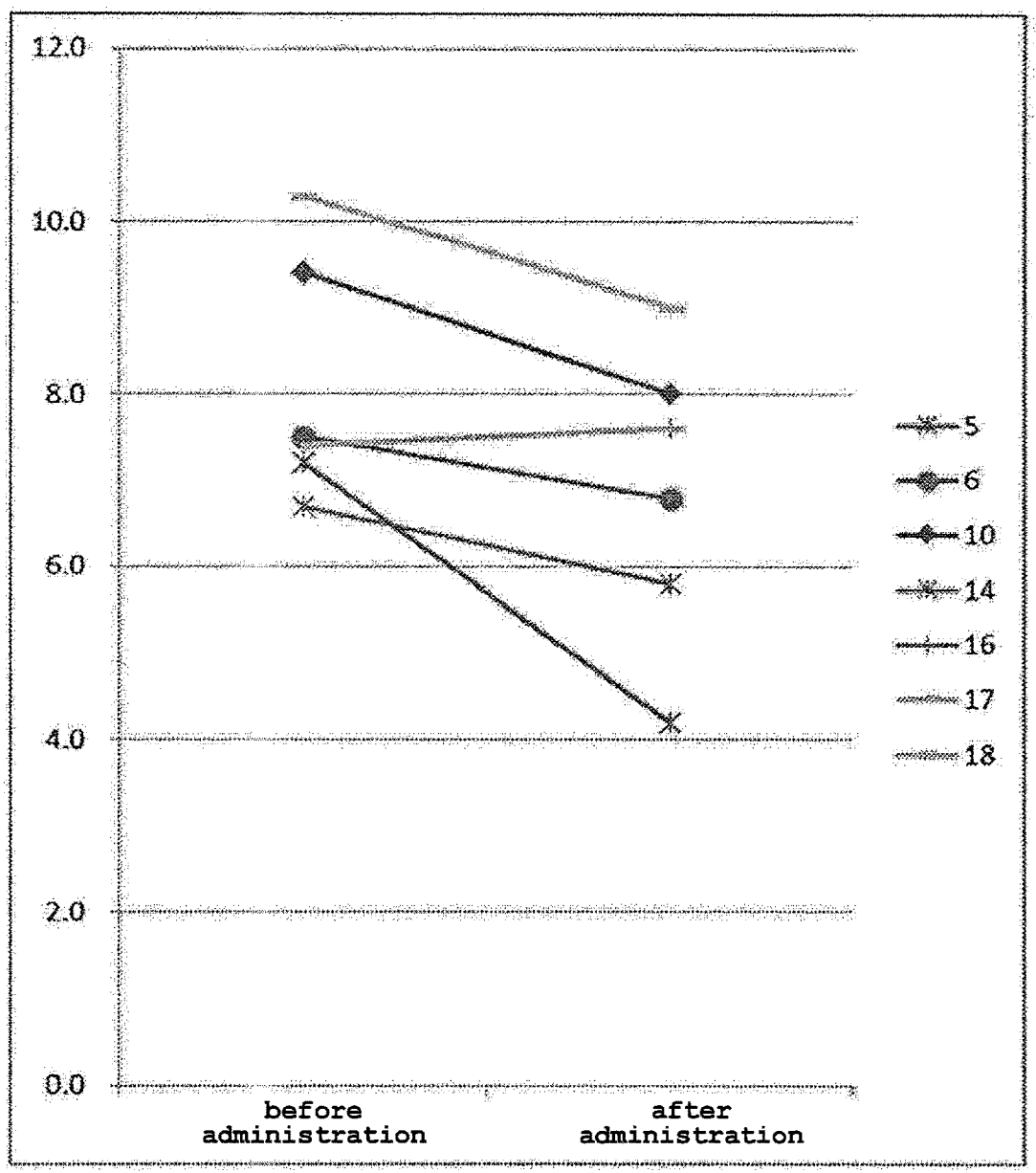
FIG. 5 shows the blood uric acid levels before and after ingestion of NTM003 strain in a human test of a human who showed a comparatively high (not less than 6.5 mg/dL) uric acid level before administration.

The results of the uric acid level of 18 test subjects are shown in FIG. 4. In addition, the results only of the test subjects who showed a comparatively high (not less than 6.5 mg/dL) uric acid level before the start of ingestion are shown in FIG. 5. In the results of the test subjects who showed a comparatively high uric acid level, a significant difference of P value<0.05 was found between the mean of before ingestion and that of after ingestion. That is, while the uric acid level of a human who showed a normal uric acid level does not show a tendency toward variation, hyperuricemia could be improved by ingestion of a *lactobacillus* powder in a human who showed a comparatively high uric acid level.

Example 4 In Vivo Test Relating to Fatty Liver Suppressive Action of *Lactobacillus*

Using a model mouse of obesity and/or diabetes, KKAy mouse, the effect of NTM003 strain was evaluated. KKAy mice (KKAy/TaJcL, male, 4-week-old) were acclimated on a commercially available normal feed (ND) for one week, and divided into two groups as shown in Table 3.

TABLE 3

| test group | feed + test substance | n |
|---|---|---|
| group 1 | HFD60 (93%) + HFD60 improved feed (5%) + starch (2%) | 8 |
| group 2 | HFD60 (93%) + HFD60 improved feed (5%) + NTM003 powder (2%) | 8 |

(Feed and a Test Substance)

HFD60 was purchased from Orientalbio Co., Ltd. HFD60 improved feed was prepared by Orientalbio Co., Ltd. according to the composition shown in Table 4. As the test substance, starch or NTM003 powder was used. As the NTM003 powder, the *lactobacillus* powder prepared in Production Example 1 of Example 2 was adjusted with starch to a concentration of $2 \times 10^{11}$ CFU/g and the obtained powdered bacterium was used. The feed+test substance to be ingested freely by group 1 and group 2 in the test group was prepared by kneading each material at the ratio described in Table 3.

TABLE 4

| component | amount (%) |
|---|---|
| milk casein | 16.4 |
| L-cystine | 0.25 |
| maltodextrin | 6 |
| α-cornstarch | 10.11 |
| sucrose | 5.5 |
| soybean oil | 2 |
| lard | 48.2 |
| powder cellulose | 6.61 |
| AIN-93G-MX | 3.5 |
| calcium carbonate | 0.18 |
| AIN-93-VM | 1 |
| choline bitartrate | 0.25 |
| total | 100 |

(Breeding (Test))

Each group was allowed to freely ingest the feed+test substance at 4 g/day for 42 days.

Figure 6:
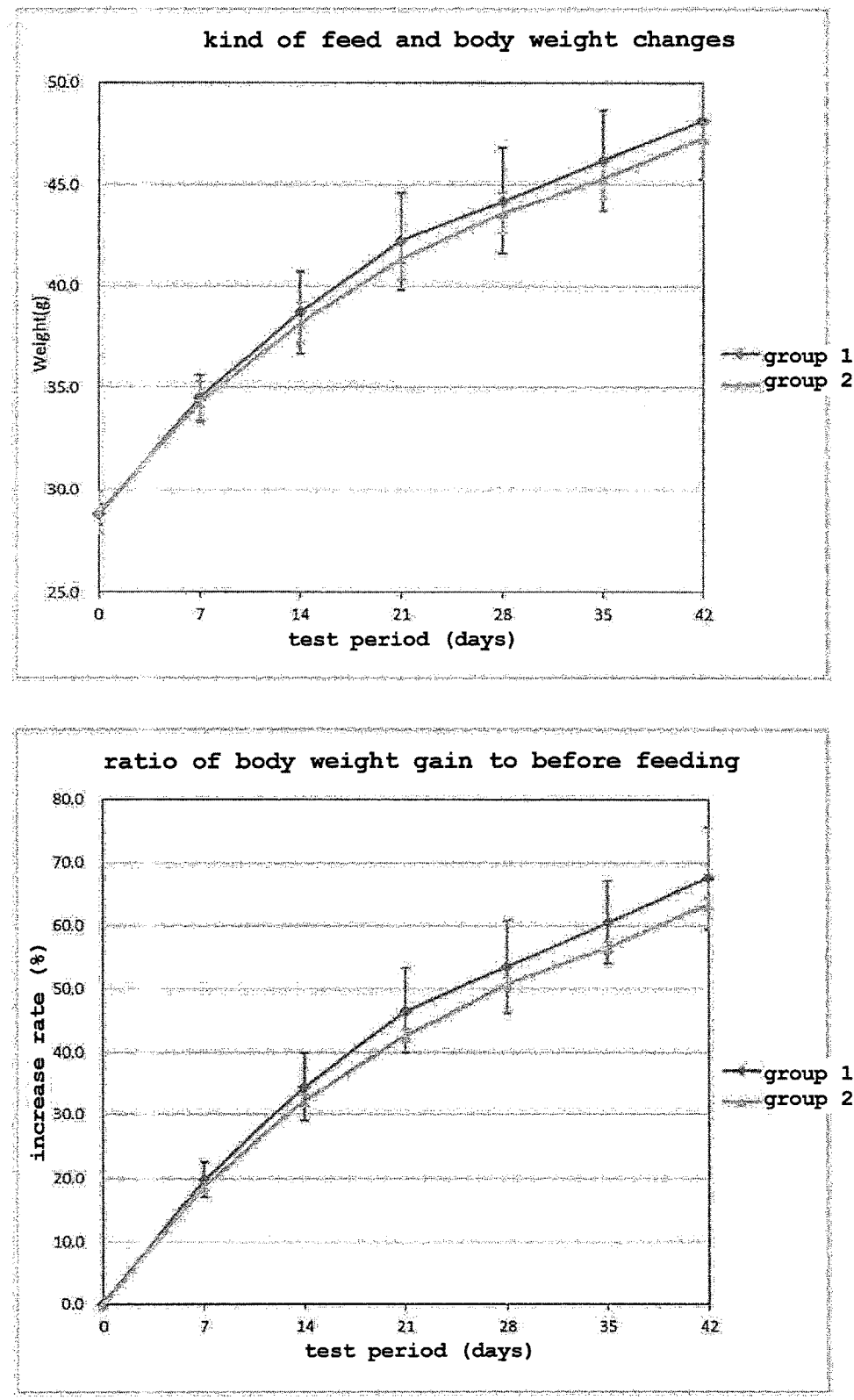
FIG. 6 shows body weight changes of a mouse model of obesity up to 42 days after giving a high-fat diet and *lactobacillus*.
Figure 7:
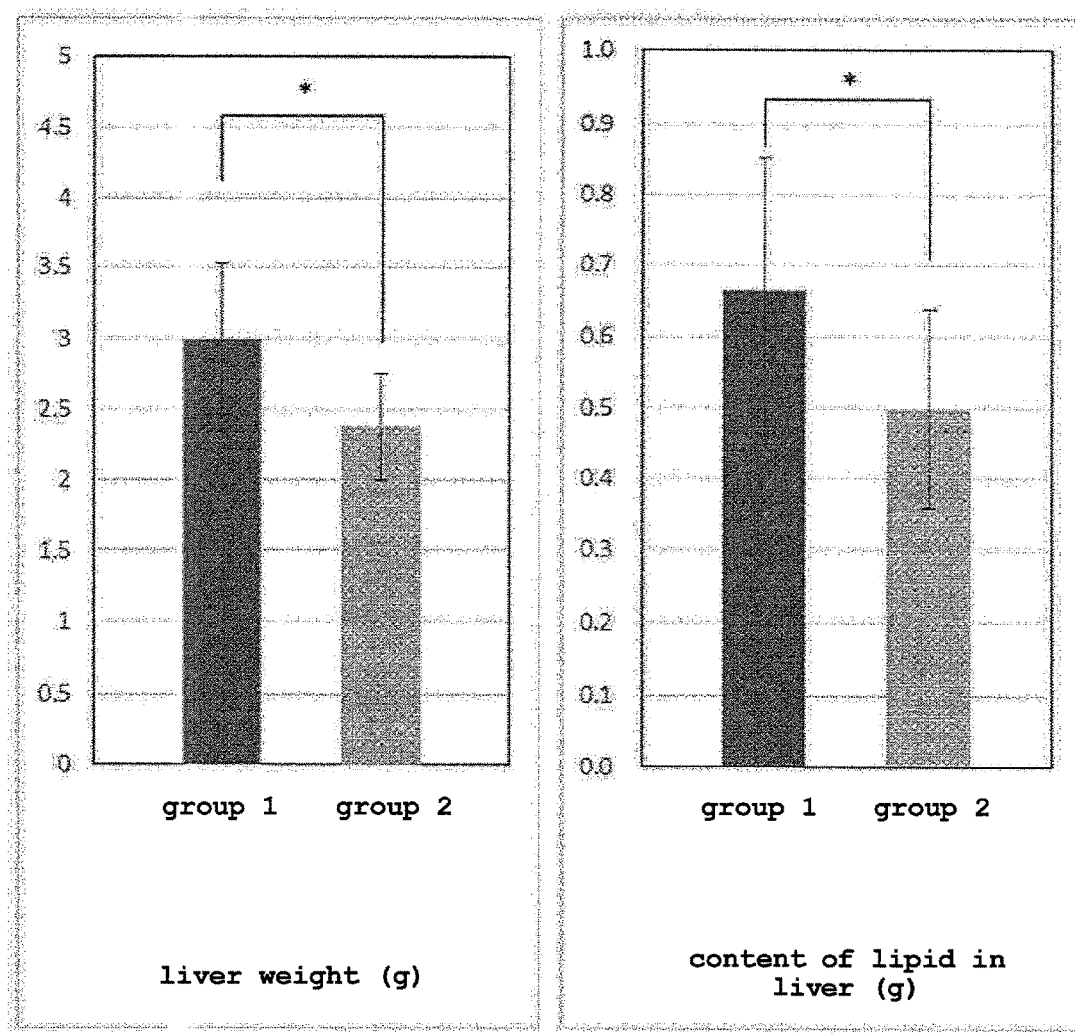
FIG. 7 shows the liver weight and liver lipid content of a mouse model of obesity at 42 days after giving a high-fat diet and *lactobacillus*.

The body weight of KKAy mouse was measured every week, autopsied on day 42, and organ weight, blood biochemical tests (cholesterol, neutral fats, free fatty acid), and water content of feces were measured. The body weight profile is shown in FIG. 6, and the biochemical tests on day 42 and the like are shown in Table 5. The liver weight and lipid content of the liver are also shown in FIG. 7.

TABLE 5

| name of organ | measurement items | group 1 | group 2 |
|---|---|---|---|
| liver | body weight (g) | 48.2 ± 2.9 | 47.3 ± 2.2 |
|  | weight (g) | 3.00 ± 0.53 | 2.38 ± 0.38* |
|  | lipid content (%) | 22.0 ± 3.4 | 20.8 ± 3.8 |
|  | total lipid content (g) | 0.664 ± 0.188 | 0.500 ± 0.139* |
|  | water content (%) | 48.5 ± 4.0 | 49.3 ± 3.9 |
| visceral fat [#1] | weight (g) | 1.04 ± 0.13 | 0.95 ± 0.11 |
| blood | total cholesterol (mg/dL) | 169 ± 13 | 168 ± 21 |
|  | neutral fats (mg/dL) | 319 ± 117 | 246 ± 133 |
|  | free fatty acid (mEq/L) | 1.701 ± 0.507 | 1.554 ± 0.494 |
| feces | water content (%) | 9.9 ± 2.3 | 11.2 ± 4.6 | mean ± standard deviation

Dunnett's multiple comparison test (control group>)

*p < 0.05

[#1] visceral fat weight was that of one side of groin

From the results of FIG. 7 and Table 5, group 2 that ingested NTM003 strain *lactobacillus* as a test substance showed a significantly light weight of the liver and a low lipid content of the liver, as compared to group 1, and a fatty liver suppressive action of the NTM003 strain was acknowledged.

From the above results, *Lactobacillus brevis* NTM003 strain (NITE BP-01634) was shown to be a novel *lactobacillus* concurrently having a high uric acid level improving effect and a fatty liver suppressive action.

While the present invention has been described with emphasis on preferred embodiments, it is obvious to those skilled in the art that the preferred embodiments can be modified.

The contents disclosed in any publication cited herein, including patents and patent applications, are hereby incorporated in their entireties by reference, to the extent that they have been disclosed herein.

INDUSTRIAL APPLICABILITY

The present invention has found a novel *lactobacillus* strain and clarified that the *lactobacillus* strain has plural functions to improve hyperuricemia and fatty liver. A composition containing the *lactobacillus* or a processed bacterium thereof can be applied to various fields such as pharmaceutical product, food and the like, and the present invention is industrially extremely useful.

This application is based on a patent application No. 2014-110912 filed in Japan (filing date: May 29, 2014), the contents of which are incorporated in full herein.

The invention claimed is:

1. A method of reducing blood uric acid level, weight of liver, or lipid content of the liver in a subject comprising administering to the subject an effective amount of *Lactobacillus brevis* NTM003 strain deposited with the Incorporated Administrative Agency National Institute of Technology and Evaluation (NITE) Patent Organisms Depository under Accession No. NITE BP-01634 or a freeze-dried *Lactobacillus brevis* NTM003 strain.

2. The method according to claim 1, wherein the *Lactobacillus brevis* NTM003 strain or freeze-dried *Lactobacillus brevis* NTM003 strain is orally administered at $1\times10^4$-$1\times10^{12}$ cells or an amount equivalent thereto per day to a patient with a high blood uric acid level, or a fatty liver patient.

3. The method according to claim 2, wherein the *Lactobacillus brevis* NTM003 strain is administered to the subject.

4. The method according to claim 2, wherein the freeze-dried *Lactobacillus brevis* NTM003 strain is administered to the subject.

5. The method according to claim 1, wherein the *Lactobacillus brevis* NTM003 strain is administered to the subject.

6. The method according to claim 1, wherein the freeze-dried *Lactobacillus brevis* NTM003 strain is administered to the subject.

\* \* \* \* \*

SEQUENCE LISTING

<160> NUMBER OF SEQ ID NOS: 1

<210> SEQ ID NO 1
<211> LENGTH: 1527
<212> TYPE: DNA
<213> ORGANISM: Lactobacillus brevis

<400> SEQUENCE: 1

```
agagtttgat cctggctcag gacgaacgct ggcggcatgc ctaatacatg caagtcgaac      60
gagcttccgt tgaatgacgt gcttgcactg atttcaacaa tgaagcgagt ggcgaactgg     120
tgagtaacac gtgggaaatc tgcccagaag caggggataa cacttggaaa caggtgctaa     180
taccgtataa caacaaaatc cgcatggatt ttgtttgaaa ggtggcttcg gctatcactt     240
ctggatgatc ccgcggcgta ttagttagtt ggtgaggtaa aggcccacca agacgatgat     300
acgtagccga cctgagaggg taatcggcca cattgggact gagacacggc ccaaactcct     360
acgggaggca gcagtaggga atcttccaca atggacgaaa gtctgatgga gcaatgccgc     420
gtgagtgaag aagggtttcg gctcgtaaaa ctctgttgtt aaagaagaac acctttgaga     480
gtaactgttc aagggttgac ggtatttaac cagaaagcca cggctaacta cgtgccagca     540
gccgcggtaa tacgtaggtg gcaagcgttg tccggattta ttgggcgtaa agcgagcgca     600
ggcggttttt taagtctgat gtgaaagcct tcggcttaac cggagaagtg catcggaaac     660
tgggagactt gagtgcagaa gaggacagtg gaactccatg tgtagcggtg gaatgcgtag     720
atatatggaa gaacaccagt ggcgaaggcg gctgtctagt ctgtaactga cgctgaggct     780
cgaaagcatg ggtagcgaac aggattagat accctggtag tccatgccgt aaacgatgag     840
tgctaagtgt tgggagggttt ccgcccttca gtgctgcagc taacgcatta agcactccgc     900
ctggggagta cgaccgcaag gttgaaactc aaaggaattg acggggcc gcacaagcgg     960 tggagcatgt ggtttaattc gaagctacgc gaagaacctt accaggtctt gacatcttct    1020
gccaatctta gagataagac gttcccttcg gggacagaat gacaggtggt gcatggttgt    1080
cgtcagctcg tgtcgtgaga tgttgggtta agtcccgcaa cgagcgcaac ccttattatc    1140
agttgccagc attcagttgg gcactctggt gagactgccg gtgacaaacc ggaggaaggt    1200
ggggatgacg tcaaatcatc atgccccctta tgacctgggc tacacacgtg ctacaatgga    1260
cggtacaacg agttgcgaag tcgtgaggct aagctaatct cttaaagccg ttctcagttc    1320
ggattgtagg ctgcaactcg cctacatgaa gttggaatcg ctagtaatcg cggatcagca    1380
tgccgcggtg aatacgttcc cgggccttgt acacaccgcc cgtcacacca tgagagtttg    1440
taacacccaa agccggtgag ataaccttcg ggagtcagcc gtctaaggtg ggacagatga    1500
ttagggtgaa gtcgtaacaa ggtaacc                                        1527
```